(12) United States Patent
Elistratov

(10) Patent No.: US 9,125,933 B2
(45) Date of Patent: Sep. 8, 2015

(54) BIOLOGICALLY ACTIVE FOOD ADDITIVE FOR PREVENTING CARDIOVASCULAR DISEASES AND REINFORCING THE CARDIOVASCULAR SYSTEM

(76) Inventor: Dmitriy G. Elistratov, Penza (RU)

( * ) Notice: Subject to any disclaimer, the term of this patent is extended or adjusted under 35 U.S.C. 154(b) by 324 days.

(21) Appl. No.: 13/821,117

(22) PCT Filed: Nov. 25, 2010

(86) PCT No.: PCT/RU2010/000704
§ 371 (c)(1),
(2), (4) Date: Jun. 7, 2013

(87) PCT Pub. No.: WO2011/078736
PCT Pub. Date: Jun. 30, 2011

(65) Prior Publication Data
US 2013/0243881 A1   Sep. 19, 2013

(30) Foreign Application Priority Data

Nov. 30, 2009   (RU) ................................ 2009144334

(51) Int. Cl.
| | | |
|---|---|---|
| *A61K 36/73* | (2006.01) | |
| *A61K 35/12* | (2015.01) | |
| *A61K 36/185* | (2006.01) | |
| *A61K 36/734* | (2006.01) | |
| *A23L 1/076* | (2006.01) | |
| *A23L 1/30* | (2006.01) | |
| *A61K 35/64* | (2015.01) | |

(52) U.S. Cl.
CPC ............... *A61K 36/734* (2013.01); *A23L 1/076* (2013.01); *A23L 1/3002* (2013.01); *A61K 35/64* (2013.01); *A23V 2002/00* (2013.01)

(58) Field of Classification Search
None
See application file for complete search history.

(56) References Cited

U.S. PATENT DOCUMENTS

2003/0040009 A1 *  2/2003  Denny et al. .................... 435/7.1
2006/0040911 A1 *  2/2006  Liao et al. ....................... 514/183

FOREIGN PATENT DOCUMENTS

| CN | 101249108 A * | 8/2008 |
|---|---|---|
| RU | 2000807 C1 | 10/1993 |
| RU | 2019185 C1 | 9/1994 |
| RU | 2020952 C1 | 10/1994 |
| RU | 2088250 C1 | 8/1997 |
| RU | 2104024 C1 | 2/1998 |

* cited by examiner

*Primary Examiner* — Chris R Tate
*Assistant Examiner* — Randall Winston
(74) *Attorney, Agent, or Firm* — Alexander Rabinovich

(57) ABSTRACT

The biologically active food additive comprises hawthorn flowers and/or berries and/or leaves and royal jelly in the following ingredient ratio: from 10 mass % to 90 mass % of hawthorn; from 10 to 24 mass % of royal jelly; and from 0 mass % to 70 mass % of fillers. The additive is produced in powder, tablet or capsule form, or aqueous-alcoholic extract form. The complex system of biologically active substances contained in the proposed biologically active food additive not only exerts an effect on the entire cardiovascular system, but also reduces the causes of cardiovascular diseases and improves quality of life in old age by acting on the pathology of the human body. This long-acting agent for prophylaxis and planned health improvement has no contraindications or side effects even during long-term use (more than one year).

8 Claims, No Drawings though the hawthorn content dominates in its composition, the present invention relates only to such preparations wherein the cardiovascular effect of the hawthorn is reinforced by other ingredients.

BIOLOGICALLY ACTIVE FOOD ADDITIVE FOR PREVENTING CARDIOVASCULAR DISEASES AND REINFORCING THE CARDIOVASCULAR SYSTEM

CROSS-REFERENCE TO RELATED APPLICATIONS

This application is a U.S. National phase application of the International application WO 2011/078736 A1 (PCT/RU2010/000704) and claims priority to application 2009144334 filed on Nov. 30, 2009 in the Russian Federation, both applications being hereby incorporated by reference in their entirety.

BACKGROUND OF THE INVENTION

1. Field of the Invention

The invention relates to biologically active food additives (hereinafter referred to as BAA) and is intended for rendering preventive action on the cardiovascular system.

2. Description of Related Art

Known are therapeutic preparations in the form of herbal tea for treating patients suffering from various kinds of cardiovascular system disorders (RU 2000807, Herbal Tea "CORDIS" for the Treatment of Cardiovascular Diseases"; RU 2019185, "Herbal Tea with a Sedative and Hypotensive Action"; RU 2020952, "Herbal Tea "Glaya", "Darya", "Elena" with a General Health-Improving and Antisclerotic Action"; RU 2088250, "Herbal Tea for Treating Patients with Cardiac Rhythm Disorder"; and RU 2104024, "Kasmin" Preparation for the Prevention and Treatment of Thromboses").

However, the above phytotherapeutic agents have a number of limitations. They belong to pharmaceuticals and therefore need to be prescribed and controlled by a physician, i.e., do not belong to preventive preparations having the status of the BAA.

They include a rather large number of components which, along with benefits arising from a versatile harmonic action on the body (Herbal Tea, Almaty, Kainar Publishers, 1991, 288 pp.), also imposes substantial constraints on the possibility to set up a wide-scale commercial production of such preparations. Therefore, multicomponent preparations often remain remedies of folk medicine.

By way of example, "Kasmin" according to RU 2104024, Oct. 2, 1998, belongs to such preparations. It contains Horse Chestnut seeds, root of Licorice, leaves of Peppermint or Lemon Balm, Hawthorne fruit, and Rosa fruit taken in a certain ratio and ground into 3-4 mm particles. The tea acts not only on the hemostatic system itself but also on the cardiovascular system as a whole, nervous system, lipid carbohydrate metabolism. It is administered to adults for the prevention and comprehensive treatment of thrombosis of various etiologies, thrombophlebitis, thromboembolic complications of myocardial infarction, embolic apoplexies and the like including, for the prevention of postoperative period thrombosis and also for the prevention of atherosclerosis.

The above herbal tea has a number of limitations, namely, it contains a large number of ingredients which, as noted above, presents certain organizational and technological difficulties for mass production.

The tea is intended for making an infusion dosage form so that the substances beneficial for the body are inevitably partly lost due to using only the liquid phase. In addition, it also involves a cumbersome process of preparing and inconvenience of administration for users.

BRIEF SUMMARY OF THE INVENTION

It is an object of the invention to provide a preparation meeting the status of a BAA wherein the above limitations are overcome.

The BAA has to include a minimum amount of pharmacopeia ingredients with the most pronounced therapeutic properties with respect to the cardiovascular system, along with a minimum of contraindications and side effects.

Upon ingestion, the BAA has to ensure a maximum preservation of the synergy of biologically active substances, be easy to use and store and possess high manufacturability for mass production.

The technical effect achieved using the invention lies in providing a dosed preparation meeting the status of BAA, comprising a certain amount of high performance ingredients whose synergy, on the one hand, ensures a long-lasting effect on the cardiovascular system and, on the other hand, has a wide spectrum of preventive and health promoting systemic actions. The technological aspects of the production of the BAA present no difficulties for the mass production thereof, and the consumer package enables sensory perception of the entire combination of biologically active substances and ease in use and storage.

DETAILED DESCRIPTION OF THE INVENTION

According to the present invention, a BAA for preventing or reducing the incidence of cardiovascular diseases and enhancing the cardiovascular system is provided, comprising hawthorn flowers and/or berries and/or leaves, royal jelly, and an excipient in a following ratio of the ingredients: hawthorn flowers and/or berries and/or leaves: from 61 to 90 wt. %, royal jelly: from 10 to 24 wt. %, excipients: from 0 to 29 wt. %.

The inventive preparation can be made in a powdered, tableted or capsulated form and can also be in the form of an aqueous alcoholic extract and dosage forms prepared on the basis of such extract, namely, powder, tablet and capsule.

The selection of hawthorn and royal jelly as ingredients of the biologically active food additive is motivated by the following reasons.

Hawthorn is one of the primary plants used in phytotherapeutic practice for regulating the cardiovascular activity both independently (see for example RU 2085206, "An Agent for the Treatment of Paroxysmal Tachycardia and Angioneurosis) and as a part of herbal tea (see the above referenced patent documents).

Hawthorn fruits contain tanning agents, pectins, flavonoids (quercetin, hyperoside, vitexin), anthocyans and leucoanthocyans triterpene and phytosterol-like compounds, choline, acetylcholine, ursolic, chlorogenic, caffeic, crataegus, oleanolic acids, fatty oil, sugars, trace elements such as copper, cobalt, zinc, manganese, iron, molybdenum, and others, vitamins C, PP, B1, B2, carotenoids. Such content ensures high efficiency of the fruits against various diseases, especially cardiac diseases (Minaeva V. G., Medicinal Plants of Siberia, Novosbirsk, Nauka Publishers, 1991, 431 pp.).

Hawthorn flowers and leaves contain flavonols (quercetin, quercitrin, and hyperoside), essential oil, caffeic and chlorogenic acids, acetylcholine, choline and the same trace elements as in the fruits.

Hawthorn preparations have a versatile systemic action and act practically on the entire cardiovascular system. Having an antiarrhythmic (cardiac arrhythmia is a disorder of the cardiac rate, rhythm and normal coordinated contractions in various cardiac parts and areas), cardiostimulatory, coronary vasodilating, hypotensive, and sedative action, they are used in atherosclerosis, angina, and tachycardia. Hawthorn flavonoids suppress the action of the angiotensin converting enzyme (ACE) responsible for vasoconstriction. The vasodilatory action creates conditions for a mild reduction in the arterial pressure and myocardium load, has a mild diuretic action. Data is available with regard to the hawthorn action against the atherosclerotic process in the walls of arteries. Hawthorn improves oxygen supply to the cerebral neurons. Therefore, the hawthorn preparations are indicated in case of the age-related changes of the cardiovascular system functioning and may be to the full extent referred to as the agents improving the quality of life in the elderly and old age. Hawthorn preparations are prescribed against angioneurosis, ciliary arrhythmia, paroxysmal tachycardia, hypertension, angina pectoris, extrasystole, cardiovascular insufficiency, thyrotoxicosis, atherosclerosis, insomnia, during menopause, in case of decreased immunity (M. Risman, Biologically Active Additives: the Unknown about the Known, Translated from English, Moscow, Art Business Center Publishers, 1998).

As the second ingredient, royal jelly is used in the invention. Royal jelly is an agent widely used in the folk and scientific medicine (included in the State Pharmacopeia). It has long been considered as a kind of a vital elixir and used against various diseases. Its chemical composition is so unique that one can hardly find another equally curative product. Royal jelly contains about 400 substances essential to the human body, some of them (for example, oxydecenoic acids) being naturally found only in royal jelly. The main ones of them are essential fatty and amino acids, proteins, trace elements, natural antibiotics, hormone-like substances, vitamins, and enzymes. Their proportions have been selected so as to ensure forced metabolism directed to the development of body structures and functions (Krivtsov N. I., Burmistrova L. A., Apitherapy Theory and Agents, Moscow, Comme it faut Publishers, 2007).

Although the components of the inventive preparation are known in the folk and traditional medicine, their combination in a single product in the claimed ratios is not disclosed in the prior art.

Thus, it has been unexpectedly found that the biologically active additive comprising hawthorn flowers and/or berries and/or leaves in amounts of from 61 to 90 wt. % and royal jelly in amounts of 10 to 24 wt. % exhibits a prolonged, i.e., long-lasting positive effect on the human cardiovascular system.

This unexpected effect of the use of royal jelly and hawthorn in the claimed ratios is explicable by the following. In the therapy of heart diseases, it is important to take into consideration that they are often associated with or determined by other causes, for example, hypertension, renal insufficiency, etc. Therefore, royal jelly action may, first of all, be associated with a beneficial effect on the general course of a pathological process being the main cause of the heart disease, rather than on myocardium.

There is sufficient amount of data from literature regarding the influence of royal jelly on these general systemic pathological processes (Lupachev V., Apilac in the Treatment of Coronary Atherosclerosis, Ryazan, 1965; Ludyansky E. A. et al., Apilac in Neurological Patients with Vascular Crises and Asthenia. Apitherapy Today, $2^{nd}$ Collected Volume, Rybnoye, 1993; Lyusov V. A. et al., Influence of Royal Jelly on the Course of Angina pectoris and Lipid Blood Composition in Patients with Ischemic Heart Disease//Apitherapy Today ($3^{rd}$ Collected Volume). Rybnoye,1994)

In other words, hawthorn preparations act on the "consequence" and royal jelly on the "causes" of cardiovascular diseases. It is believed that precisely this multidirectional action accounts for the high efficiency of the claimed preparation for a long time, the maximum depot action of the claimed additive being achieved just due to the claimed ratio of hawthorn and royal jelly that have been found by applicants.

It should be noted that the cardio protective action of the claimed agent is higher than that of its separate components due to the antioxidant activity of royal jelly leading to an antihypoxic effect in case of myocardial ischemia.

In case of myocarditis, royal jelly accelerates regeneration of the specific cardiac tissue along with sparing stimulation of cicatrization. Without the use of royal jelly, scarring becomes diffusive and absorbs the residues of the muscular tissue which could otherwise have regenerated. When royal jelly is introduced in amounts of from 10 to 24 wt. %, scarring proceeds slower but the scar develops smaller in return and, accordingly, the cardiac muscle becomes less damaged.

A complex system of biologically active substances contained in the proposed BAA not only acts on the cardiovascular system, showing antiarrhythmic, cardiostimulatory, coronary vasodilating, hypotensive properties favorable in atherosclerosis, angina pectoris, tachycardia, as well as sedative action, and also on the entire body, acting as a supplement to principal synthetic drugs thereby improving the quality of life in the elderly and old age. The use of this BAA will make it possible to achieve a more lasting effect than using chemical pharmaceuticals. It is necessary to remember that this preparation is not an instantaneous action agent and is unable to relieve, for example, retrosternal pain or normalize the heart rhythm. It is a long-lasting action agent for the systematic comprehensive counteracting and preventing (or reducing the incidence of) heart diseases. It is very important that no contraindications or side effects have been identified even in case of administering the BAA for a very long period (over one year).

EXAMPLES OF PREPARING THE BAA

Example 1

Ground hawthorn fruits and royal jelly were provided in the following ratio: hawthorn fruits: 90 wt. %, royal jelly: 10 wt. %. The components were mixed together to homogeneity and the final product was encapsulated.

Example 2

Ground hawthorn fruits and leaves, royal jelly and excipient (calcium stearate, sugar, starch) were provided in the following ratio: hawthorn fruits and leaves: 61 wt. %, royal jelly: 24 wt. %, excipients: 15 wt. %. The components were mixed together to homogeneity and the final product was tableted.

The invention claimed is:
1. A biologically active food additive for reducing the incidence and severity of cardiovascular diseases and enhancing the cardiovascular system, said food additive comprising:
   hawthorn, from 61 to 90 wt. %;
   royal jelly, from 10 to 24 wt. %; and
   one or more excipients, from 0 to 29 wt. %.
2. The biologically active food additive as claimed in claim 1, wherein the additive is made in a powder form.

3. The biologically active food additive as claimed in claim 1, wherein the additive is made in a capsulated form.

4. The biologically active food additive as claimed in claim 1, wherein the additive is made in a tableted form.

5. The biologically active food additive as claimed in claim 1, wherein the additive is made in an aqueous alcoholic form.

6. The biologically active food additive as claimed in claim 1, wherein the hawthorn comprises hawthorn flowers.

7. The biologically active food additive as claimed in claim 1, wherein the hawthorn comprises hawthorn berries.

8. The biologically active food additive as claimed in claim 1, wherein the hawthorn comprises hawthorn leaves.

* * * * *